United States Patent
Brown-Augsburger et al.

(10) Patent No.: US 7,820,179 B2
(45) Date of Patent: Oct. 26, 2010

(54) PEGYLATED PTH AS PTH RECEPTOR MODULATORS AND USES THEREOF

(75) Inventors: Patricia Lea Brown-Augsburger, Fishers, IN (US); Wayne David Kohn, Avon, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 12/440,619

(22) PCT Filed: Oct. 4, 2007

(86) PCT No.: PCT/US2007/080367

§ 371 (c)(1), (2), (4) Date: Mar. 10, 2009

(87) PCT Pub. No.: WO2008/048784

PCT Pub. Date: Apr. 24, 2008

(65) Prior Publication Data

US 2009/0253630 A1    Oct. 8, 2009

Related U.S. Application Data

(60) Provisional application No. 60/829,383, filed on Oct. 13, 2006.

(51) Int. Cl.
*A61K 38/29* (2006.01)
*A61K 39/00* (2006.01)
*C07K 14/635* (2006.01)

(52) U.S. Cl. ............... 424/198.1; 514/12; 530/324

(58) Field of Classification Search .......... None
See application file for complete search history.

(56) References Cited

U.S. PATENT DOCUMENTS

| | | | |
|---|---|---|---|
| 4,179,337 A | 12/1979 | Davis et al. | |
| 4,656,250 A | 4/1987 | Morita et al. | |
| 4,771,124 A | 9/1988 | Rosenblatt et al. | |
| 5,393,869 A | 2/1995 | Nakagawa et al. | |
| 5,556,940 A | 9/1996 | Willick et al. | |
| 5,717,062 A | 2/1998 | Chorev et al. | |
| 5,747,456 A | 5/1998 | Chorev et al. | |
| 5,814,603 A | 9/1998 | Oldenburg et al. | |
| 5,840,837 A | 11/1998 | Krstenansky et al. | |
| 5,856,138 A | 1/1999 | Fukuda | |
| 5,955,574 A | 9/1999 | Dong | |
| 6,110,892 A | 8/2000 | Barbier et al. | |
| 6,316,410 B1 | 11/2001 | Barbier et al. | |
| 6,472,505 B1 | 10/2002 | Condon et al. | |
| 6,569,993 B1 | 5/2003 | Sledeski et al. | |
| 6,756,480 B2 | 6/2004 | Kostenuik et al. | |
| 6,921,750 B2 | 7/2005 | Dong | |
| 7,022,815 B1 | 4/2006 | Gardella et al. | |
| 2004/0060386 A1 | 4/2004 | Hsieh | |
| 2004/0220094 A1 | 11/2004 | Skinner | |
| 2005/0009147 A1 | 1/2005 | Bauer et al. | |
| 2005/0026839 A1 | 2/2005 | Gardella | |
| 2005/0124537 A1 | 6/2005 | Kostenuik et al. | |
| 2005/0148763 A1 | 7/2005 | Sekimori et al. | |
| 2006/0058230 A1 | 3/2006 | Chorev et al. | |

FOREIGN PATENT DOCUMENTS

| | | |
|---|---|---|
| EP | 293158 | 5/1988 |
| EP | 477885 | 9/1991 |
| EP | 748817 | 6/1996 |
| EP | 1477496 | 11/2004 |
| JP | 63060940 | 3/1988 |
| JP | S 63-60940 | 3/1988 |
| WO | WO 94/02510 | 2/1994 |
| WO | WO 95/11988 | 5/1995 |
| WO | WO 96/40193 | 12/1996 |
| WO | WO 97/02834 | 1/1997 |
| WO | WO 98/05683 | 2/1998 |
| WO | WO 98/14478 | 4/1998 |
| WO | WO 98/30590 | 7/1998 |
| WO | WO 99/46283 | 9/1999 |
| WO | WO 99/52933 | 10/1999 |
| WO | WO 99/57139 | 11/1999 |
| WO | WO 0121643 | 3/2001 |
| WO | WO 0123521 | 4/2001 |
| WO | WO 0181415 | 11/2001 |
| WO | WO 03009804 | 2/2003 |
| WO | WO 03105772 | 12/2003 |
| WO | WO 2004060386 | 7/2004 |
| WO | WO 2004060965 | 7/2004 |
| WO | WO 2005072277 | 12/2004 |
| WO | WO 2004103273 | 8/2005 |

OTHER PUBLICATIONS

Na, Dong Hee, et al., "Capillary Electrophoretic Characterization of PEGylated Human Parathyroid Hormone With Matrix-Assisted Laser Desorption/Ionization Time-Of-Flight Mass Spectrometry," *Analytical Biochemistry* 331:322-328, Aug. 14, 2004.
Branden, Carl, et al., "Introduction to Protein Structure," p. 13-14, Garland Publishing, Inc., 1991.

*Primary Examiner*—Robert Landsman
*Assistant Examiner*—Bruce D Hissong
(74) *Attorney, Agent, or Firm*—MaryAnn Wiskerchen

(57) ABSTRACT

Pharmaceutical compositions and methods are provided for the treatment and prevention of bone loss diseases including osteoporosis in a mammal.

13 Claims, No Drawings

PEGYLATED PTH AS PTH RECEPTOR MODULATORS AND USES THEREOF

This application claims the benefit of U.S. Provisional Application Ser. No. 60/829,383 filed Oct. 13, 2006 and PCT Application Serial No. PCT/US2007/080367 filed Oct. 4, 2007, both of which are expressly incorporated herein by reference in their entirety.

FIELD OF THE INVENTION

The present invention relates to parathyroid hormone receptor (PTHR) modulator compounds and to methods of making and using them.

BACKGROUND OF THE INVENTION

Bone degenerative diseases such as osteoporosis occur in a substantial portion of the senior adult population. Osteoporosis encompasses a heterogeneous group of disorders that represent a major risk for bone fractures, and a substantial burden on the health care system. Billions of dollars are spent annually on medical care for the treatment of osteoporosis. Clinically, osteoporosis is characterized by diminished bone mass, decreased bone mineral density (BMD) and bone mineral content (BMC), and loss of bone architecture resulting in decreased bone strength and increased risk of bone fracture.

While a number of antiresorptive agents including calcitonin, bisphosphonates, estrogen, and SERMs prevent further bone loss, they do not rebuild bone once it has been lost. The first FDA approved anabolic bone building agent for the treatment of osteoporosis is human PTH(1-34), also known as teriparatide, which is marketed under the brand name FORTEO® (Eli Lilly and Company, Indianapolis, Ind.). PTH or PTH(1-34) is thought to exert its effects through receptor-mediated activation of two intracellular signaling pathways via (1) adenylate cyclase and protein kinase A, and (2) phospholipase C and protein kinase C. PTH(1-34) builds bone mass, restores bone architecture, and reduces the risk of vertebral and non-vertebral bone fractures in osteoporotic patients who are at high risk of fracture. (R. Neer, NEJM, 344:1434, 2001). As a peptide product, PTH(1-34) requires daily subcutaneous injections. International Publication Number WO2004/060386 discloses an enormous genus of PTH/PTHrP modulators comprising a vehicle that cause greater hypercalcemic response than PTH(1-34).

There remains a need for novel, therapeutic PTH analogs that demonstrate bone building efficacy as reflected by increased bone mineral content (BMC) and/or bone strength while preferably maintaining a hypercalcemia effect similar to, or less than, that of the current PTH(1-34) therapeutic and which requires less frequent administration than PTH(1-34). The compounds of the present invention satisfy these needs and provide related advantages.

SUMMARY OF THE INVENTION

A pegylated compound of the invention is a compound with a sequence selected from the group consisting of:

(SEQ ID NO: 1)
a) Ser Val Ser Glu Ile Gln Leu Met His Asn Leu Gly Arg His Leu Ala Ser Met Glu Arg Val Glu Trp Leu Arg

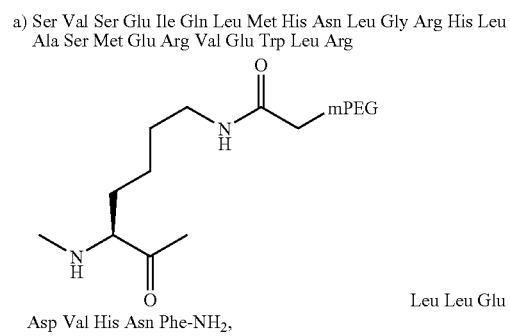

Asp Val His Asn Phe-NH₂, Leu Leu Glu (SEQ ID NO: 2)
b) Pro Val Ser Glu Ile Gln Leu Nle His Gln Arg Gly Arg His Leu Ala Ser Nle Glu Arg Val Glu Trp Leu Arg

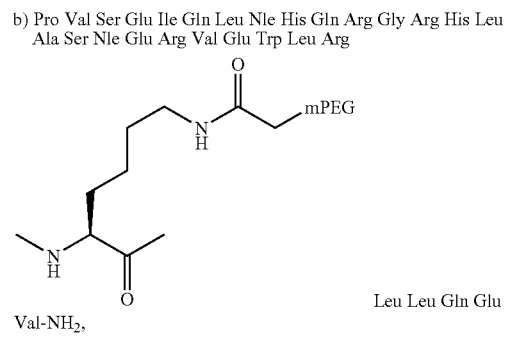

Val-NH₂, Leu Leu Gln Glu (SEQ ID NO: 3)
c) Pro Val Ser Glu Ile Gln Leu Met His Asn Leu Gly Arg His Leu Ala Ser Met Glu Arg Val Glu Trp Leu Arg

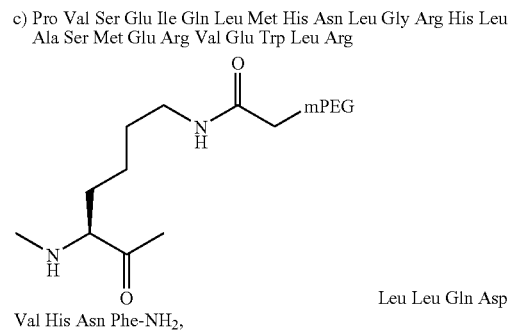

Val His Asn Phe-NH₂, Leu Leu Gln Asp (SEQ ID NO: 4)
d) Ser Val Ser Glu Ile Gln Leu Nle His Asn Leu Gly Arg His Leu Ala Ser Nle Glu Arg Val Glu Trp Leu Arg

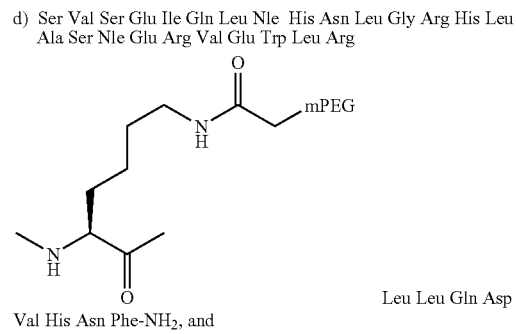

Val His Asn Phe-NH₂, and Leu Leu Gln Asp

-continued (SEQ ID NO: 5)

e) Ser Val Ser Glu Ile Gln Leu Nle His Gln Arg His Leu Ala Ser Nle Glu Arg Val Glu Trp Leu Arg

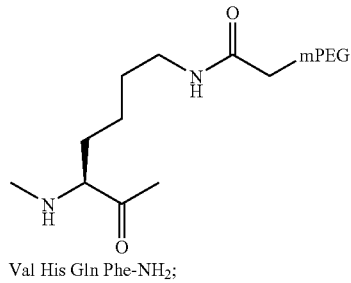

Val His Gln Phe-NH$_2$;   Leu Leu Gln Glu wherein mPEG is monomethoxy-polyethylene glycol with an average molecular weight of from 1500 to 5500 Daltons, preferably about 2000 to 5000 Daltons, more preferably about 2000 Daltons; or a pharmaceutically acceptable salt thereof.

In a preferred embodiment, the invention provides a compound with the sequence of:

(SEQ ID NO: 1)

Ser Val Ser Glu Ile Gln Leu Met His Asn Leu Gly Arg His Leu Ala Ser Met Glu Arg Val Glu Trp Leu Arg

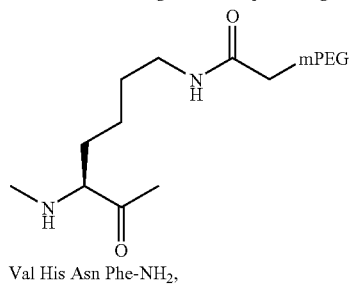

Val His Asn Phe-NH$_2$,   Leu Leu Gln Asp wherein mPEG is monomethoxy-polyethylene glycol with an average molecular weight of from 1500 to 5500 Daltons, preferably about 2000 to 5000 Daltons, more preferably about 2000 Daltons; or a pharmaceutically acceptable salt thereof.

In another preferred embodiment, the invention provides a compound with the sequence of:

(SEQ ID NO: 4)

Ser Val Ser Glu Ile Gln Leu Nle His Asn Leu Gly Arg His Leu Ala Ser Nle Glu Arg Val Glu Trp Leu Arg

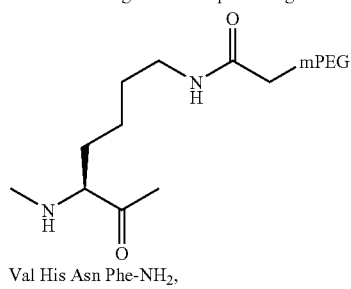

Val His Asn Phe-NH$_2$,   Leu Leu Gln Asp wherein mPEG is monomethoxy-polyethylene glycol with an average molecular weight of from 1500 to 5500 Daltons, preferably about 2000 to 5000 Daltons, more preferably about 2000 Daltons; or a pharmaceutically acceptable salt thereof.

In one embodiment, the invention provides a compound with the sequence of:

(SEQ ID NO:6)

Ser Val Ser Glu Ile Gln Leu Xaa$_8$ His Asn Leu Gly Arg His Leu Ala Ser Xaa$_{18}$ Glu Arg Val Glu Trp Leu Arg

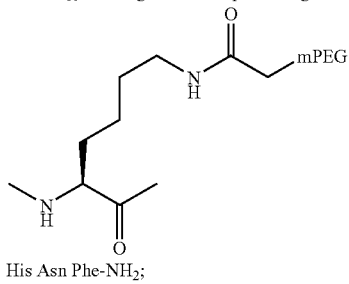

His Asn Phe-NH$_2$;   Leu Leu Gln Asp Val wherein Xaa$_8$ and Xaa$_{18}$ are Met or Xaa$_8$ and Xaa$_{18}$ are Nle; and wherein mPEG is monomethoxy-polyethylene glycol with an average molecular weight of from 1500 to 5500 Daltons, preferably about 2000 to 5000 Daltons, more preferably about 2000 Daltons; or a pharmaceutically acceptable salt thereof.

In one embodiment, the invention provides an intermediate with a sequence selected from the group consisting of:

```
                                              (SEQ ID NO: 8)
a)  Ser Val Ser Glu Ile Gln Leu Met His Asn Leu Gly
    Arg His Leu Ala Ser Met Glu Arg Val Glu Trp Leu
    Arg Lys Leu Leu Gln Asp Val His Asn Phe, (SEQ ID NO: 9)
b)  Pro Val Ser Glu Ile Gln Leu Nle His Gln Arg Gly
    Arg His Leu Ala Ser Nle Glu Arg Val Glu Trp Leu
    Arg Lys Leu Leu Gln Glu Val, (SEQ ID NO: 10)
c)  Pro Val Ser Glu Ile Gln Leu Met His Asn Leu Gly
    Arg His Leu Ala Ser Met Glu Arg Val Glu Trp Leu
    Arg Lys Leu Leu Gln Asp Val His Asn Phe, (SEQ ID NO: 11)
d)  Ser Val Ser Glu Ile Gln Leu Nle His Asn Leu Gly
    Arg His Leu Ala Ser Nle Glu Arg Val Glu Trp Leu
    Arg Lys Leu Leu Gln Asp Val His Asn Phe,
    and
```

-continued (SEQ ID NO: 12)
e) Ser Val Ser Glu Ile Gln Leu Nle His Gln Arg Gly
   Arg His Leu Ala Ser Nle Glu Arg Val Glu Trp Leu
   Arg Lys Leu Leu Gln Glu Val His Gln Phe;
or the C-terminal amide thereof.

The invention provides a method of inducing bone formation in a mammal comprising administering to a mammal in need of such treatment an effective amount of a compound of SEQ ID NO: 1, 2, 3, 4, 5, or 6 wherein mPEG is monomethoxy-polyethylene glycol with an average molecular weight of from 1500 to 5500 Daltons, monomethoxy-polyethylene glycol with an average molecular weight of from 1500 to 5500 Daltons, preferably about 2000 to 5000 Daltons, more preferably about 2000 Daltons; or a pharmaceutically acceptable salt thereof, in combination with a pharmaceutically acceptable carrier, diluent or excipient.

In one embodiment, this invention provides a compound of SEQ ID NO: 1, 2, 3, 4, 5, or 6 wherein mPEG is monomethoxy-polyethylene glycol with an average molecular weight of from 1500 to 5500 Daltons, preferably about 2000 to 5000 Daltons, more preferably about 2000 Daltons; or a pharmaceutically acceptable salt thereof, for use in therapy.

In one embodiment, this invention provides a compound of SEQ ID NO: 1, 2, 3, 4, 5, or 6 wherein mPEG is monomethoxy-polyethylene glycol with an average molecular weight of from 1500 to 5500 Daltons, preferably about 2000 to 5000 Daltons, more preferably about 2000 Daltons; or a pharmaceutically acceptable salt thereof, for use in the induction of bone formation in a mammal, preferably a human.

In one embodiment, this invention provides a compound of SEQ ID NO: 1, 2, 3, 4, 5, or 6 wherein mPEG is monomethoxy-polyethylene glycol with an average molecular weight of from 1500 to 5500 Daltons, preferably about 2000 to 5000 Daltons, more preferably about 2000 Daltons; or a pharmaceutically acceptable salt thereof, for use in treating a disease or condition in which new bone formation and/or an increase in bone mass and bone biomechanical strength would be beneficial in a mammal, preferably a human, including osteoporosis, osteopenia, bone fracture healing, spinal fusion, bone implants, joint implants, dental implants, and periodontal disease.

In one embodiment, this invention provides a compound of SEQ ID NO: 1, 2, 3, 4, 5, or 6 wherein mPEG is monomethoxy-polyethylene glycol with an average molecular weight of from 1500 to 5500 Daltons, preferably about 2000 to 5000 Daltons, more preferably about 2000 Daltons; or a pharmaceutically acceptable salt thereof, for use in treating osteoporosis in a mammal, preferably a human.

In one embodiment, this invention provides a compound of SEQ ID NO: 1, 2, 3, 4, 5, or 6 wherein mPEG is monomethoxy-polyethylene glycol with an average molecular weight of from 1500 to 5500 Daltons, preferably about 2000 to 5000 Daltons, more preferably about 2000 Daltons; or a pharmaceutically acceptable salt thereof, for use in preferably about 2000 to 5000 Daltons, more preferably about 2000 Daltons; or a pharmaceutically acceptable salt thereof.

The invention provides a method of treating a disease or condition in which new bone formation and/or an increase in bone mass and bone biomechanical strength would be beneficial in a mammal, including osteoporosis, osteopenia, bone fracture, spinal fusions, bone implants, joint implants, dental implants, and periodontal disease, comprising administering to a mammal in need of such treatment an effective amount of a compound of SEQ ID NO: 1, 2, 3, 4, 5, or 6 wherein mPEG is monomethoxy-polyethylene glycol with an average molecular weight of from 1500 to 5500 Daltons, preferably about 2000 to 5000 Daltons, more preferably about 2000 Daltons; or a pharmaceutically acceptable salt thereof.

The invention provides a method of treating osteoporosis or osteopenia in a patient comprising administering to a patient in need of such treatment an effective amount of a compound of SEQ ID NO: 1, 2, 3, 4, 5, or 6 wherein mPEG is monomethoxy-polyethylene glycol with an average molecular weight of from 1500 to 5500 Daltons, preferably about 2000 to 5000 Daltons, more preferably about 2000 Daltons; or a pharmaceutically acceptable salt thereof.

The present invention also provides a method of preventing osteoporosis or osteopenia in a mammal comprising administering to a mammal in need of such prevention an effective amount of a compound of SEQ ID NO: 1, 2, 3, 4, 5, or 6 wherein mPEG is monomethoxy-polyethylene glycol with an average molecular weight of from 1500 to 5500 Daltons, preferably about 2000 to 5000 Daltons, more preferably about 2000 Daltons; or a pharmaceutically acceptable salt thereof.

The invention provides method of treating a bone fracture in a patient comprising administering to a patient in need of such treatment an effective amount of a compound of SEQ ID NO: 1, 2, 3, 4, 5, or 6 wherein mPEG is monomethoxy-polyethylene glycol with an average molecular weight of from 1500 to 5500 Daltons, preferably about 2000 to 5000 Daltons, more preferably about 2000 Daltons; or a pharmaceutically acceptable salt thereof.

In one embodiment, the invention provides a pharmaceutical formulation comprising a compound of SEQ ID NO: 1, 2, 3, 4, 5, or 6 wherein mPEG is preventing osteoporosis in a mammal, preferably a human.

In one embodiment, the invention provides a compound of S SEQ ID NO: 1, 2, 3, 4, 5, or 6, wherein mPEG is monomethoxy-polyethylene glycol with an average molecular weight of from 1500 to 5500 Daltons, preferably about 2000 to 5000 Daltons, more preferably about 2000 Daltons; or a pharmaceutically acceptable salt thereof, for use in treating a bone fracture in a mammal, preferably a human.

The invention provides the use of a compound of SEQ ID NO: 1, 2, 3, 4, 5, or 6, wherein mPEG is monomethoxy-polyethylene glycol with an average molecular weight of from 1500 to 5500 Daltons, preferably about 2000 to 5000 Daltons, more preferably about 2000 Daltons; or a pharmaceutically acceptable salt thereof, for the manufacture of a medicament for treating a disease or condition capable of being improved or prevented by induction of bone formation.

The invention provides the use of a compound of SEQ ID NO: 1, 2, 3, 4, 5, or 6, wherein mPEG is monomethoxy-polyethylene glycol with an average molecular weight of from 1500 to 5500 Daltons, preferably about 2000 to 5000 Daltons, more preferably about 2000 Daltons; or a pharmaceutically acceptable salt thereof, for the manufacture of a medicament for the treatment of conditions in which new bone formation and/or an increase in bone mass and bone biomechanical strength would be beneficial in a mammal, preferably a human, including osteoporosis, osteopenia, bone fracture healing, spinal fusion, bone implants, joint implants, dental implants, and periodontal disease.

The invention also provides the use of a compound of SEQ ID NO: 1, 2, 3, 4, 5, or 6, wherein mPEG is monomethoxypolyethylene glycol with an average molecular weight of from 1500 to 5500 Daltons, preferably about 2000 to 5000 Daltons, more preferably about 2000 Daltons; or a pharmaceutically acceptable salt thereof, for the manufacture of a medicament for treating osteoporosis in a mammal, preferably a human.

The invention also provides the use of a compound of SEQ ID NO: 1, 2, 3, 4, 5, or 6, wherein mPEG is monomethoxypolyethylene glycol with an average molecular weight of from 1500 to 5500 Daltons, preferably about 2000 to 5000 Daltons, more preferably about 2000 Daltons; or a pharmaceutically acceptable salt thereof, for the manufacture of a medicament for preventing osteoporosis or osteopenia in a mammal, preferably a human.

The invention also provides the use of a compound of SEQ ID NO: 1, 2, 3, 4, 5, or 6, wherein mPEG is monomethoxypolyethylene glycol with an average molecular weight of from 1500 to 5500 Daltons, preferably about 2000 to 5000 Daltons, more preferably about 2000 Daltons; or a pharmaceutically acceptable salt thereof, for the manufacture of a medicament for use in treating a bone fracture in a mammal, preferably a human.

DETAILED DESCRIPTION OF THE INVENTION

Bone formation occurs during fetal development and postnatal growth and also during adult life either at a low rate as part of normal bone remodeling or at an accelerated rate in response to injury or abnormal bone loss. Bone formation involves a number of processes, including osteoblast progenitor cell proliferation, osteoblast differentiation from progenitor cells and mineralisation of matrix produced by the osteoblasts. The term "inducing bone formation" or "inducing new bone formation" is taken to mean a net increase in bone mass (e.g., as demonstrated by an increase in bone mineral content ("BMC") and/or bone biomechanical strength as determined using the method of Example 4B herein.

The term "effective amount" as used herein is a dose of a compound of the invention necessary to achieve the desired pharmacological effect.

The term "in vitro activity" refers to the activity of a compound of the invention in one or more suitable in vitro assays including, for example, the ability to activate a PTH receptor in a cell-based assay. Activity may be expressed as "$EC_{50}$" which identifies an effective concentration of a compound that results in 50% of maximal activation in the assay of choice. Any suitable in vitro assay may be used to test for binding and activation of the PTH receptor, including activation of adenylate cyclase resulting in increased cyclic AMP (cAMP) levels (see Example 3 herein). Compounds of the invention have variable agonistic activity leading to an increase in intracellular cAMP.

In its typical form, mPEG (monomethoxy polyethylene glycol) is a linear polymer with terminal hydroxyl groups having the formula $CH_3O-(CH_2CH_2O)_n-CH_2CH_2-OH$, wherein n is from about 8 to about 4000. The mPEG used in the present invention have an average molecular weight of from 1,500 to 5,500 Daltons, more preferably about 2,000 to 5,000 Daltons, more preferably about 2,000 to 2,300, even more preferably about 2,000 Daltons. Commercially available mPEG reagents (e.g., NOF SUNBRIGHT® ME-020AS) generally have some degree of polydispersity, meaning that "n" varies over a range in a roughly Gaussian distribution, preferably over a narrow range. The terminal hydrogen generally may substituted with a terminating group such as an alkyl or aromatic group. Although in the mPEG molecule the terminal hydrogen is substituted with a methoxy group, it is contemplated that the terminal hydrogen may be substituted wi8th a carbon chain of varying length, e.g. up to a 10 carbon chain, linear or branched, and still fall within the invention.

A compound with a sequence as shown in SEQ ID NOs: 8-12 may be used as an intermediate in the synthesis of a pegylated compound of the invention. Preferably a compound with a sequence as shown in SEQ ID NOs: 8-12 is in the amide form at the carboxy-terminus of the compound.

The terms "linker," "linker moiety," and "spacer" are taken herein to refer to an atom or a collection of atoms optionally used to link interconnecting moieties such as a terminus of a polymer segment and a peptide. The linker moiety is the portion of the overall polymer that contains a reactive moiety to allow for covalent attachment to a mutually reactive site on a peptide.

The term "conjugated" (or interchangeably "conjugated peptide") is taken herein to indicate a heterogeneous molecule formed by the covalent attachment of a peptide to a PEG molecule.

The term "covalent attachment" means that a peptide and a polyethylene glycol molecule are either directly covalently joined to one another, or else are indirectly covalently joined to one another through an intervening moiety or moieties, such as a linker, linker moiety, or spacer.

The pegylated compounds of the present invention can react with any of a number of inorganic and organic acids or bases to form pharmaceutically acceptable salts. Preferred pharmaceutically acceptable salts are those formed with acetate acid, citrate acid and hydrochloric acid. Especially preferred are acetate salts of the compounds of SEQ ID NO: 1, 2, 3, 4 or 5, wherein mPEG is monomethoxy-polyethylene glycol with an average molecular weight of from 1500 to 5500 Daltons, preferably about 2000 to 5000 Daltons, more preferably 2000 Daltons. Methods for preparation of pharmaceutically acceptable salts of compounds of the present invention are well known to the skilled artisan (See: Stahl et al., "Handbook of Pharmaceutical Salts: Properties, Selection and Use," VCHA/Wiley-VCH (2002); and Berge et al., *Journal of Pharmaceutical Sciences,* 66:1-19, 1977).

Bone degenerative diseases, such as osteoporosis, are characterized by diminished bone mass, decreased BMD, and loss of bone architecture resulting in decreased bone strength, and increased risk of bone fracture. Pegylated compounds of the invention may build bone mass, increase bone biomechanical strength, restore bone architecture, and reduce the risk of vertebral and non-vertebral bone fractures in osteoporotic patients who are at high risk of fracture. Thus, the pegylated compounds of the invention are useful as bone-building agents to treat or prevent bone degenerative diseases, such as osteoporosis. Moreover, the pegylated compounds of the invention are useful as bone-building agents to enhance fracture healing and stimulate bone growth at the location of bone implants, joint implants or dental implants, or for treating periodontal disease.

Suitable patients include men, women, and children suffering from bone loss conditions or bone trauma, e.g., bone fracture, in which new bone formation, an increase in bone mass, and/or an increase in bone biomechanical strength would be beneficial. For example, the compounds of the invention can be administered as a means to induce bone formation and/or increase bone mass and strength, thus reducing the risk of vertebral and non-vertebral bone fracture in a patient at risk of such fractures, including patients suffering from osteoporosis or osteopenia, for example patients having age-related osteoporosis, steroid induced osteoporosis, postmenopausal osteoporosis, idiopathic osteoporosis, and primary or secondary osteoporosis. Non-vertebral sites include, for example, hip, forearm, humerus, tibia, radius, ankle, rib, foot, pelvis, and femur.

Pegylated compounds of the invention may also be administered to a patient to enhance or accelerate vertebral and/or non-vertebral fracture healing, for example, in a patient who has suffered a trauma resulting in a bone fracture, for example due to accident or sport injury, or who has suffered a fragility fracture associated with low bone mass, including hip, forearm, humerus, tibia, radius, ankle, rib, foot, pelvis, and femur.

Compound Synthesis

Compounds of the invention may be prepared as described in the following scheme exemplified for the synthesis of a compound with SEQ ID NO: 1:

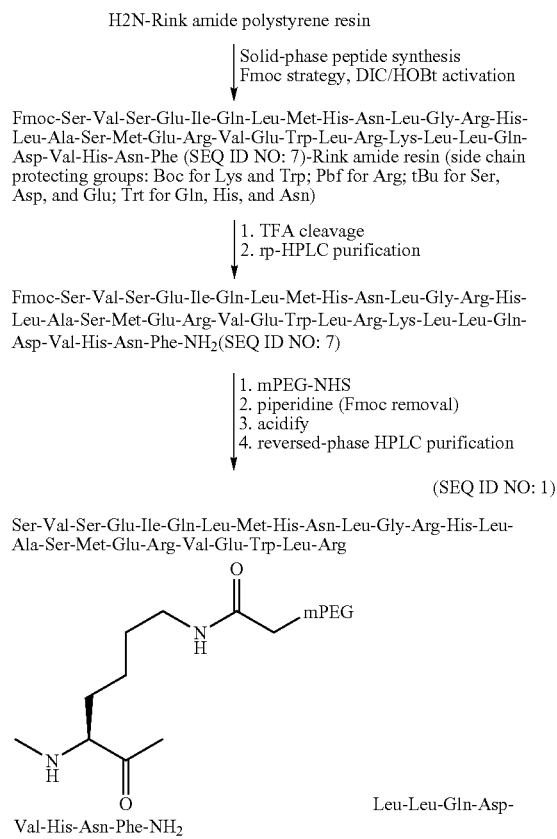

The peptide chain of the compounds of the present invention can be synthesized using standard manual or automated solid-phase synthesis procedures. Automated peptide synthesizers are commercially available from, for example, Applied Biosystems (Foster City, Calif.) and Protein Technologies Inc. (Tucson, Ariz.). Reagents for solid-phase synthesis are readily available from commercial sources. Solid-phase synthesizers can be used according to the manufacturer's instructions for blocking interfering groups, protecting amino acids during reaction, coupling, deprotecting, and capping of unreacted amino acids.

Typically, an $N^\alpha$-carbamoyl protected amino acid and the N-terminal amino acid on the growing peptide chain attached to a resin are coupled at room temperature in an inert solvent such as dimethylformamide, N-methylpyrrolidone or methylene chloride in the presence of coupling agents such as diisopropyl-carbodiimide (DIC) and 1-hydroxybenzotriazole (HOBt). The $N^\alpha$-carbamoyl protecting group is removed from the resulting peptide resin using a reagent such as trifluoroacetic acid (TFA) or piperidine, and the coupling reaction is repeated with the next desired $N^\alpha$-protected amino acid to be added to the peptide chain. Suitable amine protecting groups are well known in the art and are described, for example, in Green and Wuts, "Protecting Groups in Organic Synthesis", John Wiley and Sons, 1991. The most commonly used examples include tBoc and fluorenylmethoxycarbonyl (Fmoc). After completion of synthesis, peptides are cleaved from the solid-phase support with simultaneous side-chain deprotection using standard treatment methods under acidic conditions.

The skilled artisan will appreciate that the peptide chain of the compounds of the invention can be synthesized with either a C-terminal free acid or carboxamide. The type of derivatized polystyrene resin used for the synthesis will determine the C-terminal moiety after cleavage. A number of linkers are well known and routinely used in the art. For the synthesis of C-terminal amide peptides, resins incorporating Rink amide MBHA or Rink amide AM linkers are typically used with Fmoc synthesis, while MBHA resin is generally used with tBoc synthesis. For the generation of C-terminal acid peptides, 2-Chlorotrityl or Wang resin is typically used for Fmoc synthesis, while tBoc synthesis generally employs PAM resin. Methods for loading the first amino acid to the resin are well known in the art.

Crude peptides typically are purified using Reversed-Phase High Performance Liquid Chromatography (rp-HPLC) on C8 or C18 columns using water-acetonitrile gradients in 0.05 to 0.1% TFA. Purity can be verified by analytical rp-HPLC. Identity of peptides can be verified by mass spectrometry. Peptides can be solubilized in aqueous buffers over a wide pH range.

Conjugation of mPEG to a peptide may be carried out using well-characterized chemical synthetic reactions (See: Roberts et al., *Adv. Drug Deliv. Rev.* 54: 459-476 (2002) and Veronese, F. M., *Biomaterials* 22:405-417 (2001) or according to the manufacturer's recommendations. It is preferable that the procedure uses a molar excess of a polymer relative to the peptide to drive the reaction to completion. Excess mPEG reagent is separated from the conjugated peptide products by conventional separation methods such as rp-HPLC.

The conjugation chemistry used in preparing pegylated compounds of the invention is amide bond formation between a mPEG-carboxylate activated as, for example, an NHS(N-hydroxysuccinimide) ester and an amino group on the peptide. The linker between the mPEG and peptide is CO—CH2 (carboxy methyl). The peptide sequence of the invention is designed to contain a single Lys side chain to allow selective reaction with the incoming mPEG-NHS ester. Generally this also involves the derivatization of the amino terminus with a protecting group such as Fmoc or trifluoroacetyl, which is removed subsequently. Alternatively, the amino terminus can be left unprotected and partially selective acylation of the Lys side chain may be obtained under optimal pH and solvent conditions (See, U.S. Pat. No. 5,646,242). The amide conjugation is preferably performed with a mPEG-NHS ester derivative and an N-terminal Fmoc-protected peptide containing a single Lys (or other amine-containing amino acid) in an aqueous mixture at pH of 9 to 10 and at room temperature for 20 to 60 min. Following the conjugation, the desired conjugated peptide is recovered and purified by conventional separation methods such as rp-HPLC.

Composition

A pegylated compound of the invention may be incorporated into pharmaceutical compositions suitable for administration to a subject, particularly to a human. A pegylated compound of the invention may be administered alone or in combination with a pharmaceutically acceptable carrier, diluent, and/or excipients. Specifically, a pegylated compound of the invention may be administered in a vehicle of 20 mM $NaH_2PO_4$ in 0.9% NaCl, 3 mg/ml mannitol, pH 5. The compositions for administration are designed to be appropriate for the selected mode of administration, and pharmaceutically acceptable diluents, carrier, and/or excipients such as dispersing agents, buffers, surfactants, preservatives, solubilizing agents, isotonicity agents, stabilizing agents and the like are used as appropriate. Said compositions are designed in accordance with conventional techniques as in e.g., *Remington, The Science and Practice of Pharmacy*, 19th Edition, Gennaro, Ed., Mack Publishing Co., Easton, Pa. 1995 which provides a compendium of formulation techniques as are generally known to practitioners.

A composition comprising a pegylated compound of the invention may be administered to a subject at risk for or exhibiting pathologies as described herein using standard administration techniques including intravenous, intraperitoneal, subcutaneous, pulmonary, transdermal, intramuscular, intranasal, buccal, sublingual, or suppository administration.

The route of administration of a pegylated compound of the invention may be parenteral, oral, or by inhalation or transdermal delivery. Preferably, the pegylated compounds of the invention can be incorporated into a pharmaceutical composition suitable for parenteral administration. The term parenteral as used herein includes intravenous, intramuscular, subcutaneous, rectal, vaginal, or intraperitoneal administration. Peripheral systemic delivery by intravenous or intraperitoneal or subcutaneous injection is preferred.

A pegylated compound of the invention may be administered as an aerosol for therapeutic purposes, which are to be administered with inhalation appliances and which contain a compound of the present invention. Aerosols and methods for the synthesis thereof are described in the art.

A pegylated compound of the invention may be administered regularly, for example, once daily or once weekly. Alternatively, a pegylated compound of the invention may be administered, e.g. twice-weekly, or 3 times-weekly. Alternatively, compounds of the invention may be administered cyclically (e.g. regularly for a period of days or weeks followed by a period without administration). Preferably a pegylated compound of the invention is administered once-weekly for a period ranging from 3 months to 3 years.

The composition typically must be sterile and stable under the conditions of manufacture and storage in the container provided, including e.g. a sealed vial or syringe. Therefore, compositions may be sterile filtered after making the formulation, or otherwise made microbiologically acceptable. For parenteral administration a typical dose range for a compound of the invention is about 1 µg per week to about 10 mg per week. Preferably the human dose is in the range of 5 µg per week to about 1000 µg per week. More preferably a dose in the range of 10 µg per week to 1000 µg per week including administering 10 µg, 15 µg, 20 µg, 25 µg, 30 µg, 35 µg, 40 µg, 45 µg, 50 µg, 55 µg, 60 µg, 65 µg, 70 µg, 75 µg, 80 µg, 85 µg, 90 µg, 95 µg, or 100 µg, 150 µg, 200 µg, 250 µg, 300 µg, 500 µg, 750 µg, or 1000 µg one time per week. Although these dose ranges are set forth in units per week, it is contemplated that other time intervals may be used.

These suggested amounts of a compound are subject to a great deal of therapeutic discretion. The key factor in selecting an appropriate dose and scheduling is the clinical result obtained. Factors for consideration in this context include the particular disorder being treated, the particular mammal being treated, the clinical condition of the individual patient, the cause of the disorder, the site of delivery of the compound, the method of administration, the scheduling of administration, and other factors known to medical practitioners.

Therapeutic agents of the invention may be frozen or lyophilized for storage and reconstituted in a suitable sterile carrier prior to use. Lyophilization and reconstitution can lead to varying degrees of compound activity loss. Dosages may have to be adjusted to compensate. Generally, pH of the preparation between 4 and 8 is preferred.

A compound of the invention may be administered alone or in combination with other agents, for example, bone antiresorptive agents, including calcitonin, bisphosphonates, SERMs (e.g. raloxifene), hormone replacement therapy (HRT), calcium, Vitamin D1, Vitamin D2, Vitamin D3, Vitamin D4 and estrogen. A compound of the invention may be co-administered with another agent. Alternatively a compound of the invention may be administered sequentially with another agent; for example a compound of the invention is administered alone for a period from one week to one year followed by administration of another agent, either together with said compound or in the absence of said compound.

Articles of Manufacture

In another embodiment of the invention, an article of manufacture containing materials useful for the treatment or prevention of the diseases or conditions described above is provided. The article of manufacture comprises a container and a label. Suitable containers include, for example, bottles, vials, syringes, pens, inhalers, patches and test tubes. The containers may be formed from a variety of materials such as glass, metal or plastic. The container holds a composition of the invention which is effective for preventing or treating the diseases or conditions and may have a sterile access port (for example the container may be an intravenous solution bag or a vial having a stopper piercable by a hypodermic injection needle). The active agent in the container is a composition of the invention. The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

The following examples are offered for illustrative purposes only, and are not intended to limit the scope of the present invention in any way.

Example 1

Peptide Synthesis

Peptide synthesis is performed on Rapp AM RAM Fmoc-amide polystyrene resin (Rapp Polymere Tubingen, Germany) (substitution 0.6 to 0.7 mmol/g). The synthesis is performed using the Fmoc main-chain protecting group strategy. In addition, any amino acid side chains that are aromatic, acid, basic or highly polar are likely to be reactive. These must also be protected to prevent unwanted branched chains from forming. There are four main groups used in this way: tBoc (a tertiary butyloxycarbonyl) for Lys and Trp; Pbf (a 2,2,4,6,7-pentamethyldihydrobenzofuran-5-sulfonyl group) for Arg;

tBu (a tertiary butyl group) for Ser, Asp, and Glu; Trt (a triphenylmethyl group) for Gln, H is, and Asn). Amino acid side-chain derivatives used are: Arg(Pbf), Asn(Trt), Asp (OtBu), Cys(Trt), Gln(Trt), Glu(OtBu), His(Trt), Lys(Boc), Ser(OtBu), Trp(Boc). Coupling is carried out with approximately 10 equivalents of amino acid activated with diisopropylcarbodiimide (DIC) and hydroxybenzotriazole (HOBt) (1:1:1 molar ratio) in dimethylformamide (DMF). The Fmoc protecting group of the amino acid at position 1 is left in place to allow for selective conjugation of a Lysine side chain (see example 2 below).

Concomitant cleavage from the resin and side chain protecting group removal is carried out in a solution containing trifluoroacetic acid:triisopropylsilane:methanol:anisole 90:5:2.5:2.5 for 1.5 to 2 hours at room temperature. Cleaveage of the peptide from the Rink amide resin generates the C-terminal carboxamide form of the peptide. Peptides are precipitated with diethyl ether, redissolved in 30-40 mL of 10% acetonitrile and purified on a $C_{18}$ reversed-phase HPLC column at a flow rate of 12-15 mL/min with a linear AB gradient where A=0.05% TFA/water and B=0.05% TFA/acetonitrile. The column used is either a Waters SymmetryPrep 7 um, 19×300 mm or a Kromasil 10 um, 22×250 mm. Peptide purity and molecular weight is confirmed on an Agilent 1100 Series LC-MS system with a single quadrupole MS detector. Analytical HPLC separation is done on a Zorbax Eclipse XDB-C8, 5 micron, 4.6 mm i.d.×15 cm column with a linear AB gradient of 10 to 100% B over 15 minutes in which A=0.05% TFA/$H_2O$ and B=0.05% TFA in 60:40 $CH_3CN$:$H_2O$ and the flow rate is 1 ml/min. All peptides are purified to >95% purity and are confirmed to have molecular weight corresponding to the calculated value within 1 amu.

Example 2

Peptide Conjugation

Unconjugated peptide with an N-terminal Fmoc group in place is dissolved in 1 mL of water/acetonitrile 50/50 (36.8 mg, 4272.9 g/mol, 0.0086 mmol). A 1.5 to 2 fold molar excess of mPEG-2 kDa NHS ester (NOF Sunbright ME-020AS) is weighed out (39.7 mg, 2280 ave MW, 0.017 mmol). The peptide solution is diluted with 2 mL of 40 mM sodium borate, pH 9.8 buffer and 2 mL of acetonitrile and then added to the mPEG solution. The resultant mixture is vortexed and then stirred at room temperature. The reaction mixture is monitored by analytical reversed phase HPLC (method as described in Example 1), and typically after 20 to 30 min reaction time, shows complete disappearance of the peptide peak (at about 14.5 min) and emergence of a peak due to the peptide-PEG conjugate (at about 15.7 min). The mixture is cooled on dry ice, and 2 mL of piperidine is added to remove the N-terminal Fmoc group. The mixture is stirred at room temperature for 30 min, then cooled on dry ice and neutralized with 2 mL of glacial acetic acid (final pH=approximately 6-7). From analytical HPLC there should now be a peak at about 13.2 min due to the piperidine-fluorene adduct and a peak at about 14.25 min due to the deprotected peptide-mPEG conjugate. The mixture is diluted to about 40 mL with water and purified on either a Waters SymmetryPrep 7 μm, 19×300 mm or a Kromasil 10 μm, 22×250 mm at 12 mL/min with a 2-stage linear AB gradient of 0 to 30% B over 20 min followed by 30 to 80% B over 100 min where A=0.05% TFA/water and B=0.05% TFA/acetonitrile.

The combined fractions containing the product are lyophilized to obtain the trifluoroacetate salt form of the peptide. The product may subsequently be converted to another desired salt form by procedures known in the art. The purified peptide is quantitated by UV absorbance at 280 nm using a calculated molar extinction coefficient based on the peptide sequence. The average MW of the conjugate is (ave PEG-NHS MW+Fmoc-Peptide MW−Fmoc MW−NHS MW)=2280+4273−115−222=6216. For the example in which 36.8 mg of an unconjugated peptide is used, 34.8 mg of the pegylated peptide may be obtained. Conjugation of other peptides described in this invention, in which mPEG-NHS ester is used, is performed essentially as described above.

All data in Examples below use compounds of the invention that are C-terminal amide peptides that are mPEG-conjugated at the Lys residue of position 26 of the peptide backbone of the invention and are trifluoroacetate salts (see, e.g., SEQ ID NOs: 1-5).

Example 3

In Vitro Assay of cAMP Induction

SaOS-2 osteosarcoma cells are resuspended at $5 \times 10^5$ cells/mL in stimulation buffer [1 M HEPES/10% BSA/250 μM IBMX (3-isobutyl-1-methylxanthine, MP Biomedicals)/HBSS]. 20 μL/well of cell suspension is added per well of a 96 well black half-area assay plate (Costar) to yield $1 \times 10^4$ cells/well. Then 20 μL of diluted test compound (e.g., PTH analog of the invention, n=2) is added immediately to the cells. Test compounds are prepared as ½ log dilutions and assayed across a titration range of 3 μM to 0.1 nM. Plates are incubated for one hour at room temperature. A separate 96 well assay plate is also prepared containing cAMP as a standard curve. The cAMP standard is prepared as ½ log dilutions in stimulation buffer across a titration range of 400 to 0.0012 pmoles/well (40 μL/well) (n=6). Following the one hour incubation step, cAMP is assayed using the HTRF® (homogeneous time resolved fluorescence) cAMP dynamic 2 kit (Cisbio) according to manufacturer's directions.

When the following compounds are tested essentially as described above, they are found to induce cAMP production as tabulated below. These data demonstrate that these compounds have the potent ability to activate the PTH receptor (PTHR1) in a manner not unlike PTH.

TABLE 1

| Compounds | Average EC50 (nM) (n = 2) |
|---|---|
| SEQ ID NO: 1 with 2 kD mPEG | 7.7 |
| SEQ ID NO: 2 with 2 kD mPEG | 2.1 |
| SEQ ID NO: 4 with 2 kD mPEG | 6.9 |
| SEQ ID NO: 5 with 2 kD mPEG | 2.6 |

Example 4

In Vivo Evaluation of Conjugated Compounds

A. Young Adult Osteopenic Ovariectomized Rats

Female Sprague-Dawley rats about 3 months of age are ovariectomized, except for sham controls, and maintained on a 12 hour light/dark cycle at 22° C. with ad lib access to food (TD 89222 with 0.5% Ca and 0.4% P, Teklad, Madison, Wis.) and water. Ovariectomized (Ovx) rats are allowed to lose bone for 25 days, and then weighed and randomized into treatment groups. Treatment is by subcutaneous injection of a compound of the invention at various doses (as indicated in Table 2 below) for 1 month in a vehicle of 20 mM NaH$_2$PO$_4$ in 0.9% NaCl, 3 mg/ml mannitol, pH 5. The rats are injected with the compounds every third or fourth day to approximate once weekly administration to a human. Sham and Ovx controls are treated with the vehicle only ("sham vehicle control" and "ovx vehicle control"). Sera are collected by cardiac puncture approximately 24 hours after final injection under isoflurane anesthesia at necropsy (approximately 24 hours after the final injection), and analyzed using a clinical chemistry analyzer (Hitachi 917, Tokyo, Japan).

At necropsy, left femora are removed, cleaned of soft-tissue and stored in 50% ethanol/saline at 4° C. At room temperature, femora in 50% EtOH/saline are wrapped in Parafilm and centered with respect to the gantry for quantitative computed tomography (QCT) (Research M, Stratec). A coronal scout scan of the distal femur metaphysis is generated first in 2D before 3D analysis. QCT parameters are measured including bone mineral density (BMD, mg/ml of hydroxyl apatite) bone mineral content (BMC, mg hydroxyl apatite), and cross-sectional area (mm$^2$) as detailed previously (Sato, et al., *JPET*, 272:1252-1259, 1995).

Hypercalcemia is defined herein as the upper 97.5 percentile serum calcium value of normal ovariectomized vehicle controls for the animal type used, using clinical chemistry data and sera collected from cardiac puncture (International Federation of Clinical Chemistry, H E Solberg in Tietz Fundamentals of Clinical Chemistry, 5th edition, Burtis C A and Ashwood E R, editors, 2001, pp 251-261). The value reflecting the 97.5 percentile is 11.2 mg of calcium per dL of serum from ovx vehicle control. The "Hypercalcemic Dose", i.e., the dose at which hypercalcemia is observed 24 hours after injection of the test compound using clinical chemistry data and sera collected from cardiac puncture, is determined by interpolation, using regression analysis to fit the calcemic dose response observed 24 hours after administering the compound to ovariectomized rats.

Ovariectomy significantly reduces BMD in rats relative to sham vehicle controls over a 7.5 week period (3.5 week pretreatment phase plus 4 week treatment phase)(Sato et al. *J. Med. Chem.* 42:1-24, 1999). Pegylated compounds of the invention are able to restore BMD back to sham vehicle control levels by the end of the 4 week treatment phase. For preferred pegylated compounds of the invention, tested within the parameters of this assay, the dose required to restore BMD to Sham vehicle control levels ("BMD Dose") is not greater than the Hypercalcemic Dose. When tested essentially as described above, the compounds listed in Table 2 below are able to restore BMD of the Ovx rats to sham vehicle control level after four weeks of treatment with a certain dosage; but, a similar or higher dose of the compound is needed to induce the Hypercalcemic Dose. Factors that affect the Hypercalcemic Dose/BMD Dose ratio include, but may not be limited to, the amino acid sequence of the peptide backbone and the position of the amino acid at which the PEG is attached. Preferred compounds of the invention tested within the parameters of this assay have a Hypercalcemic Dose/BMD Dose ratio of equal to or greater than about 1.0 as shown in Table 2 below.

TABLE 2

| Compound | BMD Dose* | | Hypercalcemic Dose+ | | Hypercalcemic Dose/BMD Dose |
|---|---|---|---|---|---|
| | (nmole/kg) | (µg/kg) | (nmole/kg) | (µg/kg) | |
| SEQ ID NO: 1 with 5 kD mPEG | 3.7 | 34.3 | >32.5** | >300 | >8.8 |
| SEQ ID NO: 2 with 5 kD mPEG | 6.7 | 59.8 | >34 | >300 | >5.1 |
| SEQ ID NO: 4 with 5 kD mPEG | 31.8 | 297.9 | >32 | >300 | >1.00 |
| SEQ ID NO: 5 with 5 kD mPEG | 4.4 | 41.0 | >32.2 | >300 | >7.3 |

*dose to restore BMD to Sham control level within the assay parameters (as fit to a regression line and determined by interpolation)
+dose at which hypercalcemia is observed 24 hours after administration of the test compound within the assay parameters (as fit to a regression line and determined by interpolation)
**">" indicates that the dose stated was the highest dose tested and that hypercalcemia, as defined herein, was not reached at that dose.

B. Aged Osteopenic Ovariectomized Rats

In this example, the ability of pegylated compounds of the invention to increase biomechanical bone strength, BMD and BMC of Ovx rats to sham vehicle control levels is determined. A compound's effect on bone biomechanical strength is expected to be a better predictor of clinical efficacy than BMD. Vertebral BMD marginally predicts the clinical efficacy of osteoporosis therapies to reduce the incidence of vertebral fractures (Cummings, et al. *Am. Journal of Medicine*, 112:281-289, 2002; Sarkar et al. *J. Bone & Mineral Research* 17:1-20, 2002). Because PTH(11-34) reduces the risk of both vertebral and nonvertebral fractures (Neer et al. *NEJM*, 344:1434-1441, 2001), the efficacy of compounds of the invention are analyzed to demonstrate whether they increase bone biomechanical strength at the lumbar vertebra and at two nonvertebral sites, i.e., the femoral midshaft and the femoral neck.

Female Sprague-Dawley rats about 6 months of age are ovariectomized, except for sham controls, and maintained on a 12 hour light/dark cycle at 22° C. with ad lib access to food (TD 89222 with 0.5% Ca and 0.4% P, Teklad, Madison, Wis.) and water. Ovariectomized (Ovx) rats are allowed to lose bone for one month before treatment with compounds of the invention for two additional months. The compound to be tested is subcutaneously administered at various doses (as indicated in Table 3 below) in a vehicle of 20 mM NaH$_2$PO$_4$ in 0.9% NaCl, 3 mg/ml mannitol, pH 5, every 6 or 7 days for two months. Sham and Ovx controls are treated with the vehicle only ("sham vehicle control" and "ovx vehicle control"). Sera are then collected by cardiac puncture under isoflurane anesthesia at necropsy, and analyzed using a clinical chemistry analyzer. Lumbar vertebra L4-6 and left femora are removed, cleaned of soft-tissue and stored in 50% ethanol/saline at 4° C. At room temperature, L-5 in 50% EtOH/saline are wrapped in Parafilm and centered with respect to the QCT gantry (Research M, Stratec). A coronal scout scan of the L-5 vertebra is generated first in 2D before 3D analysis. QCT parameters are measured including BMD (mg/cc), BMC (mg), and cross-sectional area (mm$^2$). Lumbar vertebra L-5, femoral midshaft, and proximal femur are then prepared for biomechanical testing. Strength (N) is evaluated by loading the specimens to failure as described previously (Sato, et al., *Endocrinology*, 10:4330-4337, 1997).

Pegylated compounds of the invention are evaluated in this assay relative to a positive control of 3-5 µg/kg/d PTH(1-38). PTH(1-34) and PTH(1-38) are found to be indistinguishable in terms of skeletal efficacy or calcemic effects in osteopenic ovariectomized rats. It has been previously shown that rats administered 5 µg/kg/d (1 nmol/kg/d) PTH(1-34) have a systemic exposure that is about 3 times that of PTH(1-34) (i.e., FORTEO™) in humans (Tashjian and Chabner, *J. Bone Miner Res,* 17:1151-1161, 2002; Tashjian and Gagel, *J. Bone Miner Res,* 21:354-365, 2006). PTH(1-34) 5 µg/kg/d has also been previously shown to restore vertebral BMD from Ovx to sham vehicle control levels in the aged osteopenic ovariectomized rat model (Kishi et al. *Bone* 22:515-522, 1998; Kimmel et al. *Endocrinology* 132:1577-1584, 1993). This is confirmed for PTH(1-38) in this model with a dosing of 3-5 µg/kg/d.

Ovariectomy significantly reduces BMD, BMC and bone strength relative to sham vehicle controls over a three month period in aged rats. Compounds in Table 3 below, when tested essentially as described above, restore BMC of the Ovx rats to sham vehicle control levels when treated for eight weeks with the dose listed in Table 3. Further, compounds listed in Table 3, when tested essentially as described above, restore bone biomechanical strength of the Ovx rats to sham vehicle control level at one, two or three of the vertebral, midshaft and femoral neck locations tested.

For certain preferred compounds of the invention, tested within the parameters of this assay, hypercalcemia is not observed up to the maximum dose tested of approximately 110 nmol/kg. Preferred compounds of the invention, tested within the parameters of this assay, are able to restore BMD and BMC to sham vehicle control levels while also having a Hypercalcemic Dose/BMD Dose ratio equal to or greater than about 1.0, 2.0, 3.0 or 4.0, or even more preferably, greater than about 5.0, 6.0, 7.0, 8.0, 9.0, 10.0 or greater. Preferred compounds of the invention, tested within the parameters of this assay, are able to restore BMD and BMC to sham vehicle control levels while also restoring bone biomechanical strength at one, two or three of vertebral, midshaft and femoral neck locations to sham vehicle control levels. Even more preferably, compounds of the invention, tested within the parameters of this assay, are able to restore BMC and bone biomechanical strength at one or more of vertebral, midshaft and femoral neck locations to sham vehicle control levels while also having a Hypercalcemic Dose/BMD Dose ratio equal to or greater than about 1.0, 2.0, 3.0 or 4.0, or even more preferably, equal to or greater than about 5.0, 6.0, 7.0, 8.0, 9.0, 10.0 or greater.

The compound with SEQ ID NO: 4 with 2 kD mPEG (ave mw) attains sham vehicle control level strength at a dose of 11 nmol/kg for vertebral, midshaft and femoral neck sites, in the absence of hypercalcemia at the highest dose tested. Therefore, this compound with has Hypercalcemic Dose/Biomechanical Strength Dose ratio of >10 for all three sites. Similarly, SEQ ID NO: 1 with 2 kD mPEG restores vertebral and femoral neck strength to sham vehicle control levels at a dose of 11 nmol/kg, in the absence of hypercalcemia at the highest dose tested, and therefore has a Hypercalcemic Dose/Biomechanical Strength Dose ratio of >10 for these two sites. These data indicate that the sequence of the peptide backbone of a compound of the invention as well as the size of the mPEG conjugated to the peptide backbone of the compound contributes to skeletal efficacy (as reflected by BMD, BMC and strength measurements) of the compound.

TABLE 3

| Compound | Hypercalcemia Dose+ (nmol/kg) | Vertebral BMD Dose++ (nmol/kg) | Vertebral BMC Dose* (nmol/kg) | Vertebral Strength Dose** (nmol/kg) | Midshaft Strength Dose˘ (nmol/kg) | Fem Neck Strength Dose˜ (nmol/kg) |
|---|---|---|---|---|---|---|
| SEQ ID NO: 1 with 5 kD mPEG | >107 | >108 | 32 | 108 | 108 | 11 |
| SEQ ID NO: 2 with 5 kD mPEG | >112 | 112 | 34 | 32 | 108 | 32 |
| SEQ ID NO: 4 with 5 kD mPEG | >110 | >107 | 32 | 107 | 32 | 32 |
| SEQ ID NO: 5 with 5 kD mPEG | >110 | 11 | 11 | 107 | 32 | 107 |
| SEQ ID NO: 1 with 2 kD mPEG | >110 | 110 | 32 | 11 | 32 | 11 |
| SEQ ID NO: 2 with 2 kD mPEG | >117 | 34 | 34 | >117 | 117 | 34 |
| SEQ ID NO: 4 with 2 kD mPEG | >110 | 11 | 11 | 11 | 11 | 11 |
| SEQ ID NO: 3 with 2 kD mPEG | 97 | >110 | 11 | >110 | 11 | 11 |

+Dose at which hypercalcemia is observed in sera 24 hours after administration of the test compound within the assay parameters (as fit to a regression line and determined by interpolation). ">" indicates that the dose stated is the highest dose tested and that hypercalcemia, as defined herein, is not reached at that dose.
++Dose at which Sham level of vertebral bone mineral density (BMD) is achieved within the assay parameters
*Dose at which Sham level of vertebral bone mineral content (BMC) is achieved within the assay parameters
**Dose at which vertebral strength comparable to sham and the positive control (3-5 µg/kg/d PTH(1-38)) is achieved (within assay controls)
˘Dose at which midshaft strength comparable to sham vehicle control and the positive control of 3-5 µg/kg/d PTH (1-38) is achieved
˜Dose at which femoral neck strength comparable to sham vehicle control and the positive control of 3-5 µg/kg/d PTH (1-34) is achieved.

Table 4 below sets forth ratios of interest which are derived from the values in Table 3. Preferred compounds of the invention have a Hypercalcemic Dose/Vertebral BMD Dose ratio achieved within the parameters of the assay of about 1.0 or greater, more preferably equal to or greater than 3, 5, 6, 7, 8, 9 or 10. Preferred compounds of the invention have a Hypercalcemic Dose/Vertebral BMC Dose ratio achieved within the parameters of the assay of about 3.0 or greater, more preferably greater than 5, 6, 7, 8, 9 or 10. Preferred compounds of the invention have a Hypercalcemic Dose/Vertebral Strength Dose ratio achieved within the parameters of the assay of about 1.0 or greater, more preferably 3, 5, 6, 7, 8, 9 or 10 or greater. Preferred compounds of the invention have a Hypercalcemic Dose/Midshaft Strength Dose ratio achieved within the parameters of the assay of about 1.0 or greater, more preferably greater than 3, 5, 6, 7, 8, 9 or 10. Preferred compounds of the invention have a Hypercalcemic Dose/Femoral Neck Strength Dose ratio, achieved within the parameters of the assay, of about 3.0 or greater, more preferably about 5, 6, 7, 8, 9 or 10 or greater.

TABLE 4

| Compound | Hypercalcemic Dose/ Vertebral BMD Dose | Hypercalcemic Dose/ Vertebral BMC Dose | Hypercalcemic Dose/ Vertebral Strength Dose | Hypercalcemic Dose/ Midshaft Strength Dose | Hypercalcemic Dose/ Femoral Neck Strength Dose |
|---|---|---|---|---|---|
| SEQ ID NO: 1 with 5 kD mPEG | >1.0 | >3.34 | >1.0 | >1.0 | >9.7 |
| SEQ ID NO: 2 with 5 kD mPEG | >1.0 | >3.14 | >3.34 | >1.0 | >3.34 |
| SEQ ID NO: 4 with 5 kD mPEG | >1.02 | >3.43 | >1.02 | >3.43 | >3.43 |
| SEQ ID NO: 5 with 5 kD mPEG | >10.0 | >10.0 | >1.02 | >3.43 | >10.0 |
| SEQ ID NO: 1 with 2 kD mPEG | >1.0 | >3.43 | >10.0 | >3.43 | >10.0 |
| SEQ ID NO: 2 with 2 kD mPEG | >3.4 | >3.4 | 1 | >1 | >3.4 |
| SEQ ID NO: 4 with 2 kD mPEG | >10.0 | >10.0 | >10.0 | >10.0 | >10.0 |
| SEQ ID NO: 3 with 2 kD mPEG | >0.9 | 8.8 | >0.9 | 8.8 | 8.8 |

Example 5

A compound of the invention with SEQ ID NO: 1, wherein the mPEG to which it is conjugated is a 2 kD mPEG, is directly compared to a compound of the invention with SEQ ID NO: 1, wherein the mPEG to which it is conjugated is a 5 kD mPEG. Aged osteopenic ovariectomized rats are permitted to lose bone for one month before dosing (nmol/kg as in Table 5 and 6) every 6 days with vehicle alone, or the 2 kD pegylated SEQ ID NO: 1 compound or the 5 kD pegylated SEQ ID NO: 1 compound for 8 weeks. Table 5 displays the average serum calcium (mg/dL) values 24 hours after dosing. Table 6 displays the average BMD (mg/cc).

Animals dosed with either compound have normal serum calcium levels 24 hours after dosing. However, the compound with the 2 kD mPEG has less effect on serum calcium while exhibiting better BMD skeletal efficacy at low, middle and high doses than does the compound with the 5 kD mPEG. These data demonstrate that the 2 kD pegylated compound is similar to the 5 kD pegylated compound in skeletal efficacy while having lower serum calcium effects.

TABLE 5

| Dose (nmol/kg) | Serum Calcium (mg/dL) | | | |
|---|---|---|---|---|
| | Sham | Ovx | PEG 2 kD | PEG 5 kD |
| 0 | 10.69 | 10.68 | | |
| 11 | | | 10.45 | 10.86 |
| 32 | | | 10.38 | 10.79 |

TABLE 5-continued

| Dose (nmol/kg) | Serum Calcium (mg/dL) | | | |
|---|---|---|---|---|
| | Sham | Ovx | PEG 2 kD | PEG 5 kD |
| 108 | | | | 11.03 |
| 110 | | | 10.25 | |

TABLE 6

| Dose (nmol/kg) | Vertebral BMD (mg/cc) | | | |
|---|---|---|---|---|
| | Sham | Ovx | PEG 2 kD | PEG 5 kD |
| 10.3 | 625 | 544 | | |
| 11 | | | 590 | 567 |
| 32 | | | 603 | 589 |
| 108 | | | | 612 |
| 110 | | | 623 | |

Example 6

PTH(1-34) in Aged Osteopenic Ovariectomized Rats

Six-month old ovariectomized Sprague-Dawley rats are maintained on a 12 hr light/dark cycle at 22° C. with ad lib access to food (TD 89222 with 0.5% Ca and 0.4% P, Teklad, Madison, Wis.) and water. Ovariectomized rats are allowed to lose bone for 1 month, before treatment with rhPTH (1-34) for the following 3 months. The aged osteopenic ovariectomized rats are injected subcutaneously, weekly, with 0, 10 or 30 μg/kg human PTH(1-34) for 12 weeks. Sham and ovx controls are injected with the vehicle only. Lumbar vertebra are excised at necropsy and analyzed by micro-CT (Stratec), and then prepared for biomechanical testing. Strength in Newtons, (N), is evaluated by loading vertebra specimens to failure. Significance with respect to ovx vehicle controls is indicated by * in Table 7 below (Fishers PLSD, P<0.05). Model data are provided in Table 7 below.

Relative to Ovx vehicle controls, PTH(1-34) up to 30 ug/kg (7 nmol/kg) has no significant effect on vertebral BMD or vertebral biomechanical strength in osteopenic ovariectomized rats after 12 weeks of treatment. Serum calcium is normal when measured approximately 24 hours after the last dose. In comparison to data shown hereinabove, compounds of the invention have superior vertebral BMD and biomechanical vertebral strength relative to weekly PTH (1-34).

TABLE 7

Skeletal Efficacy of Weekly Dosing of PTH(1-34)

| VERTEBRAL BMD: | | Average BMD |
|---|---|---|
| Group | Dose (μg/kg) | mg/mL |
| Sham | 0 | 605* |
| Ovx | 0 | 512 |
| PTH(1-34) | 10 | 534 |
| PTH(1-34) | 30 | 529 |

| VERTEBRAL STRENGTH: | | Average Load |
|---|---|---|
| Group | Dose (ug/kg) | to Failure (N) |
| Sham | 0 | 277* |
| Ovx | 0 | 210 |
| PTH(1-34) | 10 | 222 |
| PTH(1-34) | 30 | 243 |

Example 7

PTH Receptor Internalization

The kinetics of PTHR1 (PTH Receptor 1) internalization for compounds of the invention are determined following ligand binding to membrane receptors. HEK 293 cells are transfected with PTHR-emGFP plasmid (Invitrogen).

The cells are seeded at 7,000 cells/well, 100 μL/well into clear bottomed, black, 96 well plate coated with poly-D lysine. 24 hours after being seeded into the 96 well plate, the cells are dosed with 10 μL of a compound to be tested, at final concentrations of 100 nM at staggered time points from 0 minutes to 3 hours. Media is aspirated at end point of dosing. Cells are fixed with 100 μL Prefer (Anatech, Battle Creek, Mich.) for 30 minutes. Prefer is aspirated from the cells, and cells are washed three times with 100 μL 1×PBS. Cells are stained with 100 μL diluted Hoechst nuclear stain (diluted in 1×PBS) for 30 minutes. Hoechst stain is aspirated and replaced with 1×PBS. Plates are stored in the dark at 4° C. until scanning. Cells are scanned within 48 hours using a Cellomics® ArrayScan. Representative data from various timepoints, set forth as percent of vehicle only control (baseline=100%), are presented in Table 8.

TABLE 8

| Compound* | 20 min | 40 min | 60 min | 180 min |
|---|---|---|---|---|
| PTH(1-38) | 166 | 177 | 224 | 175 |
| SEQ ID NO: 4 but unpegylated and lysine at amino acid 26 | 136 | 132 | 136 | 151 |
| SEQ ID NO: 4 with 2 kD mPEG | 154 | 167 | 186 | 163 |
| SEQ ID NO: 4 with 5 kD mPEG | 106 | 96 | 98 | 107 |
| SEQ ID NO: 2 but unpegylated and lysine at amino acid 26 | 126 | 114 | 139 | 139 |
| SEQ ID NO: 2 with 2 kD mPEG | 148 | 102 | 107 | 96 |
| SEQ ID NO: 2 with 5 kD mPEG | 128 | 95 | 108 | 102 |
| SEQ ID NO: 1 but unpegylated and Lysine at amino acid 26 | 106 | 126 | 113 | 142 |
| SEQ ID NO: 1 with 2 kD mPEG | 160 | 120 | 104 | 102 |
| SEQ ID NO: 1 with 5 kD mPEG | 127 | 93 | 91 | 92 |

These data show that compounds of the invention have markedly different internalization kinetics than PTH(1-38), depending on the sequence of the peptide backbone, whether or not it is pegylated, and the PEG size. Note that the unpegylated molecules have the backbone of the Sequence named with the exception that there is a lysine residue at position 26. The slower internalization kinetics indicates a reduced rate of PTHR1 receptor internalization when ligand-PTHR1 receptor complexes form using compounds of the invention, resulting in a greater magnitude of signaling in the cell after ligand binding. This is likely part of the explanation for the improved skeletal efficacy observed for forms of compounds of the invention with 2 kD PEG with weekly dosing over that observed with weekly PTH dosing.

We claim:

1. A compound with the sequence of:

(SEQ ID NO: 6)

Ser Val Ser Glu Ile Gln Leu Xaa$_8$ His Asn Leu Gly Arg His Leu Ala Ser Xaa$_{18}$ Glu Arg Val Glu Trp Leu Arg

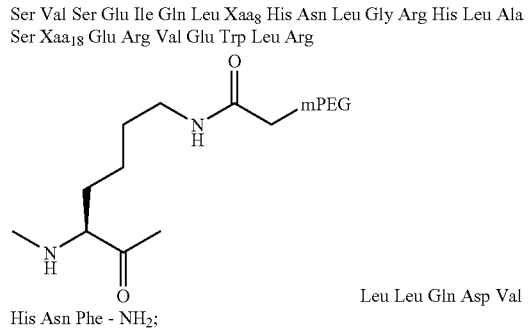

Leu Leu Gln Asp Val His Asn Phe - NH$_2$;

wherein Xaa$_8$ and Xaa$_{18}$ are Met or Xaa$_8$ and Xaa$_{18}$ are Nle; and wherein mPEG is monomethoxy-polyethylene glycol with an average molecular weight of from 1500 to 5500 Daltons; or a pharmaceutically acceptable salt thereof.

2. A compound of claim 1 having the amino acid sequence:

(SEQ ID NO: 1)

Ser Val Ser Glu Ile Gln Leu Met His Asn Leu Gly Arg His Leu Ala Ser Met Glu Arg Val Glu Trp Leu Arg

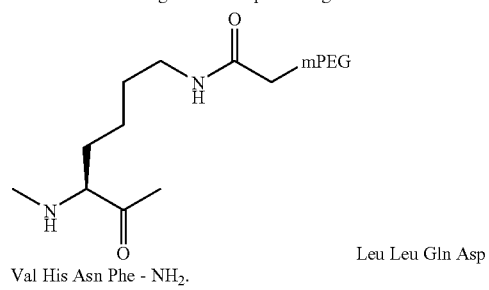

Leu Leu Gln Asp Val His Asn Phe - NH$_2$.

3. A compound of claim 1 having the amino acid sequence:

(SEQ ID NO:4)

Ser Val Ser Glu Ile Gln Leu Nle His Asn Leu Gly Arg His Leu Ala Ser Nle Glu Arg Val Glu Trp Leu Arg

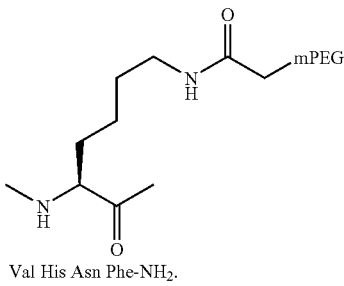

Leu Leu Gln Asp Val His Asn Phe-NH$_2$.

4. A compound selected from the group consisting of:

(SEQ ID NO: 2)

a) Pro Val Ser Glu Ile Gln Leu Nle His Gln Arg Gly Arg His Leu Ala Ser Nle Glu Arg Val Glu Trp Leu Arg

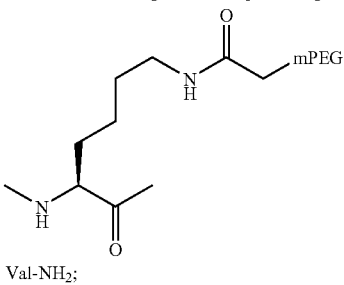

Leu Leu Gln Glu Val-NH$_2$;

(SEQ ID NO: 3)

b) Pro Val Ser Glu Ile Gln Leu Met His Asn Leu Gly Arg His Leu Ala Ser Met Glu Arg Val Glu Trp Leu Arg

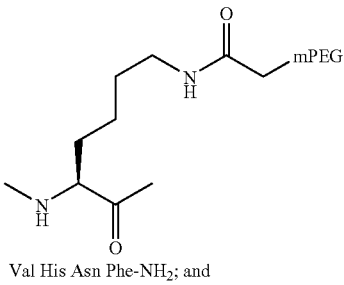

Leu Leu Gln Asp Val His Asn Phe-NH$_2$; and

-continued c) Ser Val Ser Glu Ile Gln Leu Nle His Gln Arg Gly Arg His Leu Ala Ser Nle Glu Arg Val Glu Trp Leu Arg (SEQ ID NO: 5)

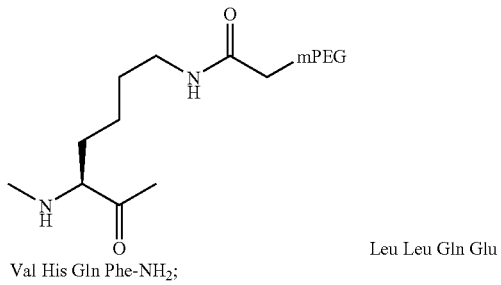

Leu Leu Gln Glu Val His Gln Phe-NH$_2$;

wherein mPEG is monomethoxy-polyethylene glycol with an average molecular weight of from 1500 to 5500 Daltons; or a pharmaceutically acceptable salt thereof.

5. The compound of claim 1, or a pharmaceutically acceptable salt thereof, wherein mPEG has an average molecular weight of from about 2000 to 5000 Daltons.

6. The compound of claim 1, or a pharmaceutically acceptable salt thereof, wherein mPEG has an average molecular weight of about 2000 Daltons.

7. The compound of claim 3, or a pharmaceutically acceptable salt thereof, wherein mPEG has an average molecular weight of about 2000 to 5000 Daltons.

8. The compound of claim 3, or a pharmaceutically acceptable salt thereof, wherein mPEG has an average molecular weight of about 2000 Daltons.

9. The compound of claim 4, or a pharmaceutically acceptable salt thereof, wherein mPEG has an average molecular weight of about 2000 to 5000 Daltons.

10. The compound of claim 4, or a pharmaceutically acceptable salt thereof, wherein mPEG has an average molecular weight of about 2000 Daltons.

11. A method of inducing bone formation in a mammal comprising administering to a mammal in need of such treatment an effective amount of a compound of claim 1, or a pharmaceutically acceptable salt thereof.

12. A method of treating osteoporosis or osteopenia in a patient comprising administering to a patient in need of such treatment an effective amount of a compound of any one of claim 1, or a pharmaceutically acceptable salt thereof.

13. A method of treating a bone fracture in a patient comprising administering to a patient in need of such treatment an effective amount of a compound of claim 1, or a pharmaceutically acceptable salt thereof.

* * * * *

UNITED STATES PATENT AND TRADEMARK OFFICE
CERTIFICATE OF CORRECTION

PATENT NO. : 7,820,179 B2
APPLICATION NO. : 12/440619
DATED : October 26, 2010
INVENTOR(S) : Patricia Lea Brown-Augsburger and Wayne David Kohn It is certified that error appears in the above-identified patent and that said Letters Patent is hereby corrected as shown below:

In Columns 31, 32 and 33, starting at column 31, line 15 and ending at column 33, line 20, please delete Claims 1 through Claims 4 and replace with the following Claims 1 through Claim 4.

1. (original) A compound with the sequence of:
Ser Val Ser Glu Ile Gln Leu Xaa$_8$ His Asn Leu Gly Arg His Leu Ala Ser Xaa$_{18}$ Glu Arg

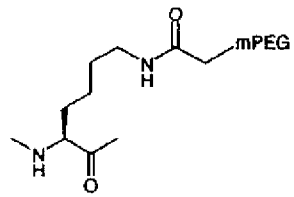

Val Glu Trp Leu Arg
Leu Leu Gln Asp Val His Asn Phe - NH$_2$ (SEQ ID NO: 6);
wherein Xaa$_8$ and Xaa$_{18}$ are Met or Xaa$_8$ and Xaa$_{18}$ are Nle; and wherein mPEG is monomethoxy-polyethylene glycol with an average molecular weight of from 1500 to 5500 Daltons; or a pharmaceutically acceptable salt thereof.

2. (original) A compound of claim 1 having the amino acid sequence:
Ser Val Ser Glu Ile Gln Leu Met His Asn Leu Gly Arg His Leu Ala Ser Met Glu Arg

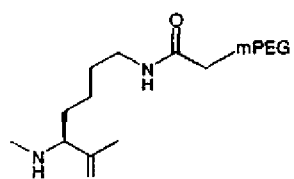

Val Glu Trp Leu Arg
Leu Leu Gln Asp Val His Asn Phe - NH$_2$ (SEQ ID NO: 1).

Signed and Sealed this
Twelfth Day of June, 2012

David J. Kappos
*Director of the United States Patent and Trademark Office*

CERTIFICATE OF CORRECTION (continued)
U.S. Pat. No. 7,820,179 B2

3. (original) A compound of claim 1 having the amino acid sequence:
Ser Val Ser Glu Ile Gln Leu Nle His Asn Leu Gly Arg His Leu Ala Ser Nle Glu Arg

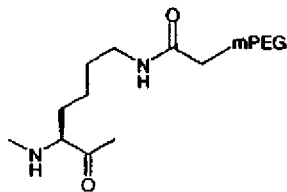

Val Glu Trp Leu Arg
Leu Leu Gln Asp Val His Asn Phe -NH$_2$ (SEQ ID NO: 4);

4. (original) A compound selected from the group consisting of:
a) Pro Val Ser Glu Ile Gln Leu Nle His Gln Arg Gly Arg His Leu Ala Ser Nle Glu Arg

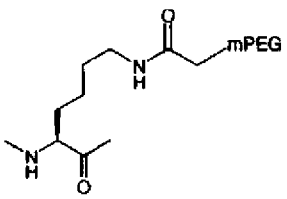

Val Glu Trp Leu Arg
Leu Leu Gln Glu Val -NH$_2$ (SEQ ID NO: 2);

b) Pro Val Ser Glu Ile Gln Leu Met His Asn Leu Gly Arg His Leu Ala Ser Met Glu Arg

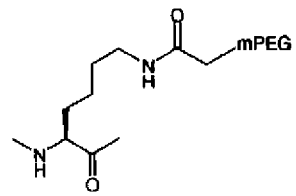

Val Glu Trp Leu Arg
Leu Leu Gln Asp Val His Asn Phe - NH$_2$ (SEQ ID NO: 3);
and c) Ser Val Ser Glu Ile Gln Leu Nle His Gln Arg Gly Arg His Leu Ala Ser Nle Glu Arg

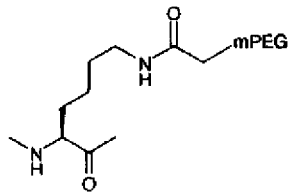

Val Glu Trp Leu Arg
Leu Leu Gln Glu Val His Gln Phe -NH$_2$ (SEQ ED NO: 5);

wherein mPEG is monomethoxy-polyethylene glycol with an average molecular weight of from 1500 to 5500 Daltons; or a pharmaceutically acceptable salt thereof.

SEQUENCE LISTING

```
<160> NUMBER OF SEQ ID NOS: 12

<210> SEQ ID NO 1
<211> LENGTH: 34
<212> TYPE: PRT
<213> ORGANISM: Artificial
<220> FEATURE:
<223> OTHER INFORMATION: SYNTHETIC CONSTRUCT
<220> FEATURE:
<221> NAME/KEY: MISC_FEATURE
<222> LOCATION: (26)..(26)
<223> OTHER INFORMATION: Xaa at position 26 is a modifed lysine
<220> FEATURE:
<221> NAME/KEY: MOD_RES
<222> LOCATION: (34)..(34)
<223> OTHER INFORMATION: Amidation

<400> SEQUENCE: 1
```

Ser Val Ser Glu Ile Gln Leu Met His Asn Leu Gly Arg His Leu Ala
1               5                   10                  15

Ser Met Glu Arg Val Glu Trp Leu Arg Xaa Leu Leu Gln Asp Val His
            20                  25                  30

Asn Phe

<210> SEQ ID NO 2
<211> LENGTH: 31
<212> TYPE: PRT
<213> ORGANISM: Artificial
<220> FEATURE:
<223> OTHER INFORMATION: SYNTHETIC CONSTRUCT
<220> FEATURE:
<221> NAME/KEY: MISC_FEATURE
<222> LOCATION: (8)..(8)
<223> OTHER INFORMATION: Xaa at position 8 is Norleucine
<220> FEATURE:
<221> NAME/KEY: MISC_FEATURE
<222> LOCATION: (18)..(18)
<223> OTHER INFORMATION: Xaa at position 18 is Norleucine
<220> FEATURE:
<221> NAME/KEY: MISC_FEATURE
<222> LOCATION: (26)..(26)
<223> OTHER INFORMATION: Xaa at position 26 is a modifed lysine
<220> FEATURE:
<221> NAME/KEY: MOD_RES
<222> LOCATION: (31)..(31)
<223> OTHER INFORMATION: AMIDATION

<400> SEQUENCE: 2

Pro Val Ser Glu Ile Gln Leu Xaa His Gln Arg Gly Arg His Leu Ala
1               5                   10                  15

Ser Xaa Glu Arg Val Glu Trp Leu Arg Xaa Leu Leu Gln Glu Val
            20                  25                  30

<210> SEQ ID NO 3
<211> LENGTH: 34
<212> TYPE: PRT
<213> ORGANISM: Artificial
<220> FEATURE:
<223> OTHER INFORMATION: SYNTHETIC CONSTRUCT
<220> FEATURE:
<221> NAME/KEY: MISC_FEATURE
<222> LOCATION: (26)..(26)
<223> OTHER INFORMATION: Xaa at position 26 is a modified Lysine
<220> FEATURE:
<221> NAME/KEY: MOD_RES
<222> LOCATION: (34)..(34)
<223> OTHER INFORMATION: Amidation

<400> SEQUENCE: 3

Pro Val Ser Glu Ile Gln Leu Met His Asn Leu Gly Arg His Leu Ala
1               5                   10                  15

Ser Met Glu Arg Val Glu Trp Leu Arg Xaa Leu Leu Gln Asp Val His
            20                  25                  30

Asn Phe

<210> SEQ ID NO 4
<211> LENGTH: 34
<212> TYPE: PRT
<213> ORGANISM: Artificial
<220> FEATURE:
<223> OTHER INFORMATION: SYNTHETIC CONSTRUCT
<220> FEATURE:
<221> NAME/KEY: MISC_FEATURE
<222> LOCATION: (8)..(8)
<223> OTHER INFORMATION: Xaa at position 8 is Norleucine
<220> FEATURE:

```
<221> NAME/KEY: MISC_FEATURE
<222> LOCATION: (18)..(18)
<223> OTHER INFORMATION: Xaa at position 18 is Norleucine
<220> FEATURE:
<221> NAME/KEY: MISC_FEATURE
<222> LOCATION: (26)..(26)
<223> OTHER INFORMATION: Xaa at position 26 is a modifed lysine
<220> FEATURE:
<221> NAME/KEY: MOD_RES
<222> LOCATION: (34)..(34)
<223> OTHER INFORMATION: Amidation

<400> SEQUENCE: 4

Ser Val Ser Glu Ile Gln Leu Xaa His Asn Leu Gly Arg His Leu Ala
1               5                   10                  15

Ser Xaa Glu Arg Val Glu Trp Leu Arg Xaa Leu Leu Gln Asp Val His
            20                  25                  30

Asn Phe

<210> SEQ ID NO 5
<211> LENGTH: 34
<212> TYPE: PRT
<213> ORGANISM: Artificial
<220> FEATURE:
<223> OTHER INFORMATION: SYNTHETIC CONSTRUCT
<220> FEATURE:
<221> NAME/KEY: MISC_FEATURE
<222> LOCATION: (8)..(8)
<223> OTHER INFORMATION: Xaa at position 8 is Norleucine
<220> FEATURE:
<221> NAME/KEY: MISC_FEATURE
<222> LOCATION: (18)..(18)
<223> OTHER INFORMATION: Xaa at position 18 is Norleucine
<220> FEATURE:
<221> NAME/KEY: MISC_FEATURE
<222> LOCATION: (26)..(26)
<223> OTHER INFORMATION: Xaa at position 26 is a modifed lysine
<220> FEATURE:
<221> NAME/KEY: MOD_RES
<222> LOCATION: (34)..(34)
<223> OTHER INFORMATION: Amidation

<400> SEQUENCE: 5

Ser Val Ser Glu Ile Gln Leu Xaa His Gln Arg Gly Arg His Leu Ala
1               5                   10                  15

Ser Xaa Glu Arg Val Glu Trp Leu Arg Xaa Leu Leu Gln Glu Val His
            20                  25                  30

Gln Phe

<210> SEQ ID NO 6
<211> LENGTH: 34
<212> TYPE: PRT
<213> ORGANISM: Artificial
<220> FEATURE:
<223> OTHER INFORMATION: SYNTHETIC CONSTRUCT
<220> FEATURE:
<221> NAME/KEY: MISC_FEATURE
<222> LOCATION: (8)..(8)
<223> OTHER INFORMATION: Xaa at position 8 is Met if Xaa at position 18
      is also Met; or Xaa at position 8 is Norleucine if Xaa at position
      18 is also Norleucine
<220> FEATURE:
<221> NAME/KEY: MISC_FEATURE
<222> LOCATION: (18)..(18)
<223> OTHER INFORMATION: Xaa at position 8 is Met if Xaa at position 18
      is also Met; or Xaa at position 8 is Norleucine if Xaa at position
      18 is also Norleucine
<220> FEATURE:
<221> NAME/KEY: MISC_FEATURE
<222> LOCATION: (26)..(26)
<223> OTHER INFORMATION: Xaa at position 26 is a modified lysine
```

```
<220> FEATURE:
<221> NAME/KEY: MOD_RES
<222> LOCATION: (34)..(34)
<223> OTHER INFORMATION: AMIDATION

<400> SEQUENCE: 6

Ser Val Ser Glu Ile Gln Leu Xaa His Asn Leu Gly Arg His Leu Ala
1               5                   10                  15
Ser Xaa Glu Arg Val Glu Trp Leu Arg Xaa Leu Leu Gln Asp Val His
            20                  25                  30
Asn Phe

<210> SEQ ID NO 7
<211> LENGTH: 34
<212> TYPE: PRT
<213> ORGANISM: Artificial
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Modified with FMOC

<400> SEQUENCE: 7

Ser Val Ser Glu Ile Gln Leu Met His Asn Leu Gly Arg His Leu Ala
1               5                   10                  15
Ser Met Glu Arg Val Glu Trp Leu Arg Lys Leu Leu Gln Asp Val His
            20                  25                  30
Asn Phe

<210> SEQ ID NO 8
<211> LENGTH: 34
<212> TYPE: PRT
<213> ORGANISM: Artificial
<220> FEATURE:
<223> OTHER INFORMATION: SYNTHETIC CONSTRUCT
<220> FEATURE:
<221> NAME/KEY: MOD_RES
<222> LOCATION: (34)..(34)
<223> OTHER INFORMATION: May or may not be amidated

<400> SEQUENCE: 8

Ser Val Ser Glu Ile Gln Leu Met His Asn Leu Gly Arg His Leu Ala
1               5                   10                  15
Ser Met Glu Arg Val Glu Trp Leu Arg Lys Leu Leu Gln Asp Val His
            20                  25                  30
Asn Phe

<210> SEQ ID NO 9
<211> LENGTH: 31
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (8)..(8)
<223> OTHER INFORMATION: Xaa at position 8 is Norleucine
<220> FEATURE:
<221> NAME/KEY: MISC_FEATURE
<222> LOCATION: (18)..(18)
<223> OTHER INFORMATION: Xaa at position 18 is Norleucine
<220> FEATURE:
<221> NAME/KEY: MOD_RES
<222> LOCATION: (31)..(31)
<223> OTHER INFORMATION: May or may not be amidated
```

```
<400> SEQUENCE: 9

Pro Val Ser Glu Ile Gln Leu Xaa His Gln Arg Gly Arg His Leu Ala
1               5                   10                  15

Ser Xaa Glu Arg Val Glu Trp Leu Arg Lys Leu Leu Gln Glu Val
            20                  25                  30

<210> SEQ ID NO 10
<211> LENGTH: 34
<212> TYPE: PRT
<213> ORGANISM: Artificial
<220> FEATURE:
<223> OTHER INFORMATION: SYNTHETIC CONSTRUCT
<220> FEATURE:
<221> NAME/KEY: MOD_RES
<222> LOCATION: (34)..(34)
<223> OTHER INFORMATION: MAY OR MAY NOT BE AMIDATED

<400> SEQUENCE: 10

Pro Val Ser Glu Ile Gln Leu Met His Asn Leu Gly Arg His Leu Ala
1               5                   10                  15

Ser Met Glu Arg Val Glu Trp Leu Arg Lys Leu Leu Gln Asp Val His
            20                  25                  30

Asn Phe

<210> SEQ ID NO 11
<211> LENGTH: 34
<212> TYPE: PRT
<213> ORGANISM: Artificial
<220> FEATURE:
<223> OTHER INFORMATION: SYNTHETIC CONSTRUCT
<220> FEATURE:
<221> NAME/KEY: MISC_FEATURE
<222> LOCATION: (8)..(8)
<223> OTHER INFORMATION: Xaa at position 8 is Norleucine
<220> FEATURE:
<221> NAME/KEY: MISC_FEATURE
<222> LOCATION: (18)..(18)
<223> OTHER INFORMATION: Xaa at position 18 is Norleucine
<220> FEATURE:
<221> NAME/KEY: MOD_RES
<222> LOCATION: (34)..(34)
<223> OTHER INFORMATION: May or may not be amidated

<400> SEQUENCE: 11

Ser Val Ser Glu Ile Gln Leu Xaa His Asn Leu Gly Arg His Leu Ala
1               5                   10                  15

Ser Xaa Glu Arg Val Glu Trp Leu Arg Lys Leu Leu Gln Asp Val His
            20                  25                  30

Asn Phe

<210> SEQ ID NO 12
<211> LENGTH: 34
<212> TYPE: PRT
<213> ORGANISM: Artificial
<220> FEATURE:
<223> OTHER INFORMATION: SYNTHETIC CONSTRUCT
<220> FEATURE:
<221> NAME/KEY: MISC_FEATURE
<222> LOCATION: (8)..(8)
<223> OTHER INFORMATION: Xaa at position 8 is Norleucine
<220> FEATURE:
<221> NAME/KEY: MISC_FEATURE
<222> LOCATION: (18)..(18)
<223> OTHER INFORMATION: Xaa at position 18 is Norleucine
<220> FEATURE:
<221> NAME/KEY: MOD_RES
<222> LOCATION: (34)..(34)
<223> OTHER INFORMATION: May or may not be amidated
```

```
<400> SEQUENCE: 12

Ser Val Ser Glu Ile Gln Leu Xaa His Gln Arg Gly Arg His Leu Ala
1               5                   10                  15

Ser Xaa Glu Arg Val Glu Trp Leu Arg Lys Leu Leu Gln Glu Val His
            20                  25                  30

Gln Phe
```